United States Patent [19]

Chin

[11] Patent Number: 4,671,278
[45] Date of Patent: Jun. 9, 1987

[54] SCALP HEMOSTATIC CLIP AND DISPENSER THEREFOR

[75] Inventor: Albert K. Chin, Irving, Tex.

[73] Assignee: Thomas J. Fogarty, Palo Alto, Calif.

[21] Appl. No.: 691,416

[22] Filed: Jan. 14, 1985

[51] Int. Cl.⁴ .............................................. A61B 17/12
[52] U.S. Cl. .................................................... 128/325
[58] Field of Search .................. 128/325, 326, 334 R, 128/337; 72/410; 29/243.56; 128/346

[56] References Cited

U.S. PATENT DOCUMENTS

| | | | |
|---|---|---|---|
| 3,802,437 | 4/1974 | Kees ..................................... | 128/325 |
| 4,217,902 | 8/1980 | March .............................. | 128/337 X |
| 4,427,008 | 1/1984 | Transve ................................. | 128/325 |
| 4,508,253 | 4/1985 | Green .................................... | 227/19 |
| 4,530,453 | 7/1985 | Green .................................... | 227/19 |

FOREIGN PATENT DOCUMENTS

| | | | |
|---|---|---|---|
| 2730691 | 1/1978 | Fed. Rep. of Germany ...... | 128/325 |
| 01280 | 4/1984 | World Int. Prop. O. .......... | 128/325 |

Primary Examiner—C. Fred Rosenbaum
Attorney, Agent, or Firm—Limbach, Limbach & Sutton

[57] ABSTRACT

Apparatus and method for hemostatically clipping an incision edge with normally biased spring clips. A magazine containing a plurality of said clips and means for conveying said clips through the magazine. A method for gathering the incision edge within a bridge, over and past which, the clip is forced thereby engaging the flesh member between the jaws of said clip.

8 Claims, 7 Drawing Figures

SCALP HEMOSTATIC CLIP AND DISPENSER THEREFOR

TECHNICAL FIELD OF THE INVENTION

This invention relates generally to apparatus and methods used in neurosurgery. In particular, improved hemostatic clips and clip dispensers, as well as methods of use thereof, are within the field of this invention.

BACKGROUND OF THE INVENTION

During surgery, an incision in the flesh is made. The incision edges begin to bleed. Before the remainder of the surgical procedure can be attempted the bleeding at the incision edges must be brought under control. The most well known and commonly used method of achieving hemostasis involves the use of pressure at the site of the incision. This pressure constricts the capillaries, minimizing the amount of bleeding along the incision edges. In neurological surgery the same method is used. An incision is made and metal or plastic clips are clamped along the scalp incision edge to achieve hemostasis while the remainder of the surgical procedure is performed. One type of clip currently in use is called the Raney clip. The Raney clip is a plastic spring clip with jaws on one side and a slot on the other. The applier has two prongs on one end of a scissor-like device. These prongs are inserted into the slot on the back side of the Raney clip. When the applier handle is squeezed the prongs at the other end force open the jaws of the clip. The open jaws of the Raney clip are then positioned on the edge of the scalp incision which has been elevated from the underlying skull. When the applier handle is relaxed, the Raney clip jaws clamp along the incision edge. The prongs then can be removed from the slot so that another Raney clip can be loaded.

For each incision, several Raney clips must be placed. However, only one clip can be applied at a time, making the placement process tedious and time consuming. Each clip must be properly oriented and then loaded onto the applier. In a surgical procedure of this type, time is of the essence; an unclipped incision edge continues to bleed, making the successive steps of the procedure more difficult. The clip dispenser which is the subject of this invention avoids the disadvantages of Raney-type appliers because this clip dispenser allows an entire row of clips to be advanced into position along the scalp incision without the need for reloading its applying means. This improved clip and dispenser eliminates the tedious and time consuming steps made necessary by having to reload a Raney clip after each placement.

It is therefore an object of this invention to provide an apparatus for dispensing hemostatic clips which is simple and easy to use, without need for reloading after each clip is placed.

It is therefore a further object of this invention to provide a magazine for rapidly dispensing a plurality of hemostatic clips along an incision edge.

It is another object of this invention to provide an apparatus which is both sterilizable and disposable.

SUMMARY OF THE INVENTION

Broadly, the subject of this invention is a clip dispenser and its method of use, which has a magazine capable of holding and orienting a number of clips such that when advanced toward the distal end of the magazine, the jaws of said clips will be opened. At the distal end of the magazine there are guides which gather the scalp incision edge to be clipped. The opened clips are advanced toward the distal end of the magazine by conveying means. Further advancement positions the distal clip on the guides. The final step in clip placement occurs as the distal clip is pushed into position on the scalp incision edge by the next clip in line. When the distal clip is forced off the guides onto the scalp edge, the next clip is automatically positioned on the prongs, ready for its successive application to the scalp incision. The flesh is engaged between the now closed clip jaws, achieving hemostasis along the incision edge.

In one of the preferred embodiments, the magazine has a channel with a bottom surface and two side walls. Attached to each sidewall is a wedge. When the magazine is loaded, the wedges are positioned between the two opposing surfaces of the clip. At the distal end, the wedges' width is substantially equivalent to the width of the guides so that the clips can be pushed toward and onto the guides for clip placement. Conveying means are used to exert a force on the last clip, closest the near end, in the direction of the guides. This force is then transferred from clip to clip, as the jaws at the front of the clip successively impart force to the rear face of the next clip. The methods which are the subject of this invention involve the use of the improved apparatus to close an incision, inducing hemostasis at the incision edge. Guides or bridges are used to gather the flesh member along the incision edge. The clip is directed towards and past the bridge which forces the clips to engage the flesh member between its now closed jaws. The process can be repeated along both of the incision edges thereby implanting a series of hemostatic clips along the edges to completely close the incision during a surgical procedure.

BEST MODE FOR CARRYING OUT THE INVENTION

Figure 1:
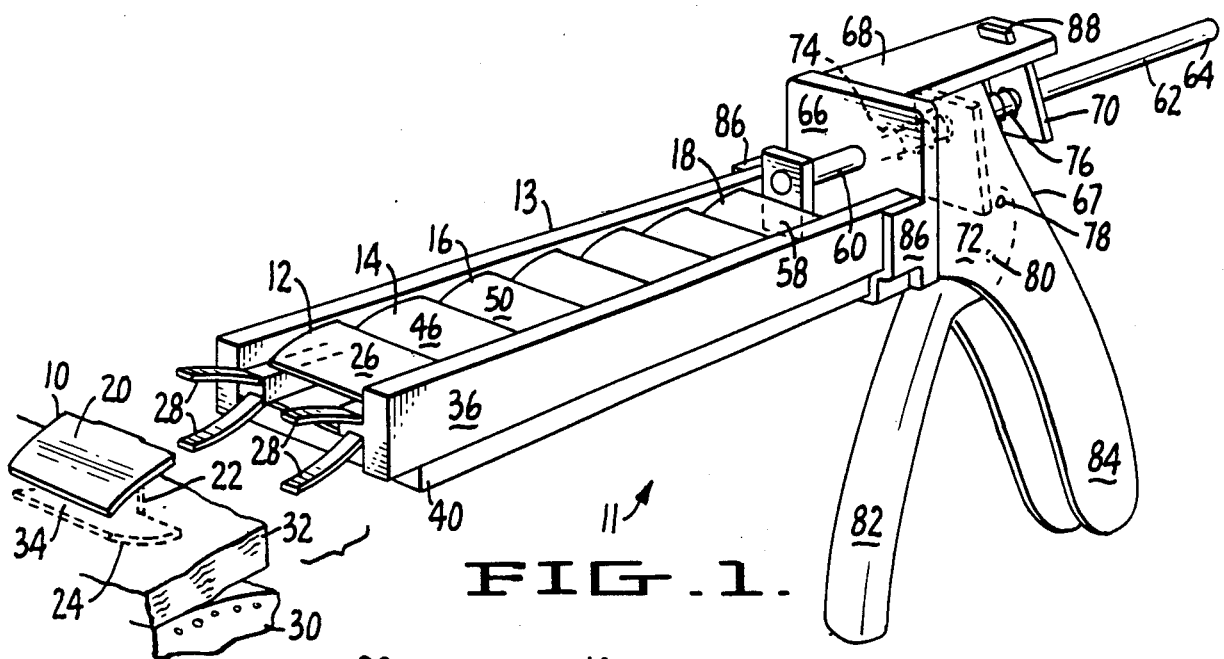
FIG. 1 is a perspective view of a scalp hemostatic clip dispenser.

This particularly preferred embodiment of the invention is described with reference to FIGS. 1-6. Beginning with FIG. 1, the clip apparatus is shown in relation to its useful environment. During neurosurgery, a scalpel is used to cut through the flesh. An incision edge 32 is formed in the flesh covering the skull 30. The blood vessels and capillaries in the incision edge 32 must be controlled to prevent an excessive amount of blood from obstructing subsequent steps of the surgical procedure. A first hemostatic clip 10 has been placed to reduce the bleeding at the incision edge 32. The upper surface 20 and lower surface 24 of the first hemostatic clip exert pressure on the hemostatic site 34 restricting blood flow to the incision edge 32; this pressure causes hemostasis. The force at the hemostatic site 34 must be controlled so that the blood vessels and capillaries in the incision edge 32 will not be permanently deformed. The configuration of the rear face 22 is important in biasing the surfaces together and in the magnitude of the force exerted at the hemostatic site 34. It can be seen from FIG. 1, that the incision edge 32 must be lifted up and away from the skull 30 for proper clip placement. The lower surface 24 of the first hemostatic clip must be able to advance between the incision edge 32 and skull 30 so that the clip 10 is properly placed relative to the incision edge 32.

To facilitate clip placement along the incision edge 32, a dispenser 11 has guides 28 at the end where the clips are issued. These guides 28 have upper and lower members which gather the incision edge 32 and lift it up and away from the skull 30. As the second clip 12, third clip 14 and fourth clip 16 advance towards the guides 28, the opposing surfaces of the clips are opened wider so that when the clips reach the guides 28, the clips slide onto the upper and lower members of the guides 28. The incision edge 32 is between the open jaws of the clips and, as additional force is exerted along the dispenser's long axis by the plate 58 and bar 62, the clip is forced off of the guides 28 with the incision edge 32 between its upper surface 20 and lower surface 24. To place a series of these clips, e.g., clips 10, 12, 14, 16, and 18, along an incision edge 32, these clips must move along the dispenser in a highly defined spatial orientation so that the force conveyed by the plate 58 directs the clips towards and past the guides 28 and so that their opposing surfaces will be sufficiently open to accommodate the incision edge 32.

Figure 3:
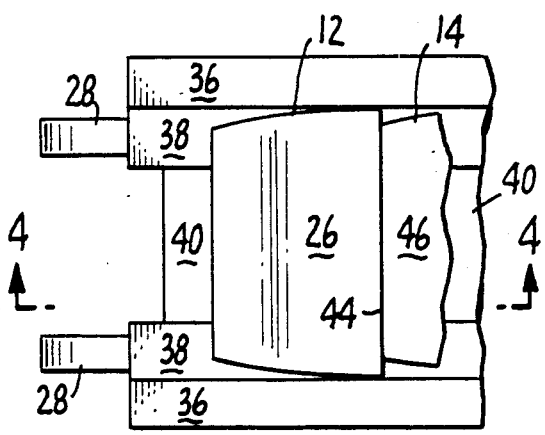
FIG. 3 is a fragmentary plan view of the guide end of the scalp hemostatic clip dispenser.
Figure 4:
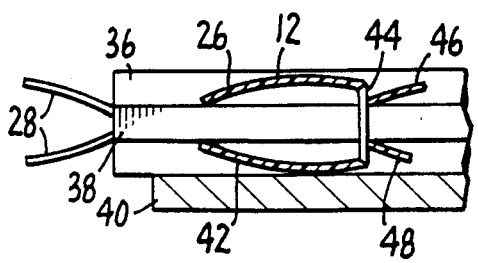
FIG. 4 is an elevational section taken along the line 4—4 in FIG. 3.

This orientation requirement is met in this embodiment of the dispenser 11 by the cooperation of the clips 12, 14, 16 and 18 and the magazine 13 as shown in FIG. 1, 3 and 4. The magazine 13 is defined by two sidewalls 36 and a lower surface 40. As discussed above, the guides 28 are at that end of the magazine 13 from which the clips are issued. The other end of the magazine is held in place by magazine bracket 86. The magazine 13 is placed flush against the front face of the base 66 to accommodate the plate 58 at the end of the bar 62 so that the clips may be advanced towards the guides 28. Referring now to FIG. 3, attached to the inside of the magazine side walls 36 are wedges 38 running the entire length of the magazine 13. The clips are loaded into the magazine 13 so that the wedges 38 are positioned between the slightly open jaws of the two opposing surfaces. This can be more clearly seen with reference to FIG. 4 where the wedges 38 are found between the upper surface 26 and lower surface 42 of the second hemostatic clip 12. In this preferred embodiment, the wedges 38 are divergent such that they are narrow at the end of the magazine 13 closest the front face of the base 66 and widest, equivalent to the base of the guides 28, at the distal end. As shown in FIG. 3, the clips 12 and 14 are in contact along the rear face 44 of the second hemostatic clip and the front edge of the third hemostatic clip 14. All of the clips in the magazine 13 are arranged such that the front of each clip abuts the rear face of the previous clip.

Although in this preferred embodiment wedges 38 are used, there are other embodiments within the scope of this invention. For example, the wedges 38 need not have divergent surfaces but instead could have parallel surfaces, which would then be called rails. Although constituting one preferred embodiment, these rails do not have to be attached to the inner surface of the magazine side walls 36. Other embodiments can be developed; however, the clip design may need to be changed to accommodate other rail means.

Figure 2:
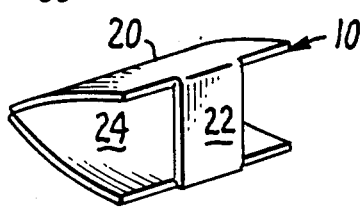
FIG. 2 is a perspective view of the scalp hemostatic clip.

In the embodiments of the invention where the wedges 38 have divergent or parallel surfaces attached to the side walls of the magazine, a clip 10, as shown in FIG. 2, is capable of accommodating the rail or wedge 38. The clip 10 is defined by generally rectilinear upper 20 and lower 24 surfaces. Connected between these opposing rectilinear surfaces is a rear face 22. This rear face 22 provides the biasing force which brings the two surfaces 20 and 24 together along the opposite edge of the surfaces. The rear face 22 and its connection to the opposing surfaces 20 and 24 provide the biasing force which clamps the incision edge 32. The magnitude of the biasing force is an important design criteria, varying between the lower limit of a minimum hemostatic pressure and an upper limit of blood vessel and capillary wall damage. Portions of the rear face 22 also define rail or wedge accommodating means. In this particularly preferred embodiment, these means comprise square excised areas on either side of the face 22. These excised areas permit the wedges 38 to pass through the clip 10 and between the jaw formed by the surfaces 20 and 24. This clip design, as in FIG. 2, also facilitates the movement of the clips in the magazine 13. Ejecting force is applied to the clip 18 by a bar plate 58 in the direction of the guides 28, shown in FIG. 1. Referring to FIG. 2, this force is applied to the rear face 22 of the clip. The force is transmittted to successive clips by abutment of the front edge of each clip, defined by the intersection of the upper 20 and lower 24 surfaces, with the rear face 22 of the next succession clip. The design of the rear face 22 is important for this transmission of forces, since deformation in this face could result in variance from the desired spacial orientation of the clips in the magazine.

The force which advances the clips along the magazine 11 is provided by trigger operated bar forwarding mechanism. The illustrated mechanism is similar to that used in conventional caulking guns. In this mechanism, a bar 62, having the bar plate 58 at one end, passes through the front face of the base 66, a first bar spring 74, a bar forwarding plate 72, a rear face of the base 67, a second bar spring 76 and a bar lock 70. The bar lock 70 fits through bar lock slot 88 in the bar lock support 68. When the bar lock 70 is in the position shown in FIG. 1, the bar 62 cannot be retracted in the direction of the bar free end 64, but it can be advanced towards the plate end 60 by action of the bar forwarding plate 72. When the bar lock 70 is pushed against the second bar spring 76, towards the base handle 84, the bar 62 can be retracted in the bar free end 64 direction. The bar forwarding plate 72 is activated by a trigger 82 through a trigger bar 78. When the trigger 82, which is pivotally joined to the base handle at a pivot pin 80, is squeezed closer to the base handle 84, the trigger bar 78 forces the bar forwarding plate 72 against the first bar spring 74 towards the front face of the base 66. The bar 62, which passes through the aperture in the bar forwarding mechanism 72, is pushed towards its plate end 60. This force is then transmitted to the clip 18 via the bar plate 58. Each squeeze of the trigger 82 pushes the bar 62 and bar plate 58 a discrete distance closer to the guide 28 end of the magazine 13. When it is desired to reload the magazine 13, the bar 62 and plate 58 can be retracted by pushing the bar lock 70 towards the rear face of the base 67, and then pulling the bar 62 at its free-end 64 away from the base face 67.

Figure 5:
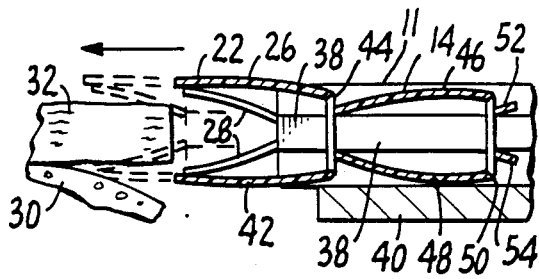
FIG. 5 is another elevational section in a subsequent position in clip placement.
Figure 6:
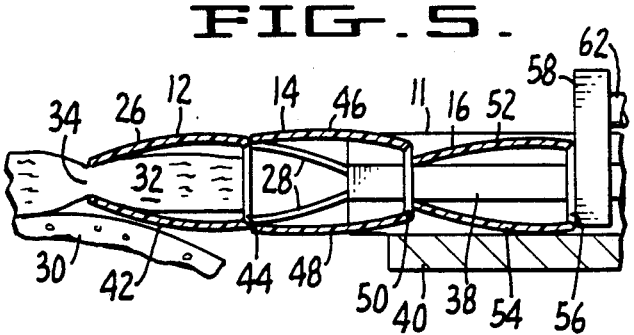
FIG. 6 is another elevational section in a further step in clip placement.
Figure 7:
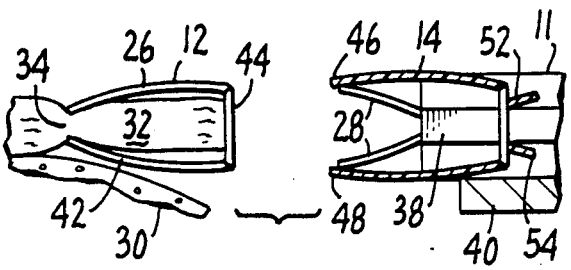
FIG. 7 is an elevational section of a final position in clip placement.

The improved method of the invention may be seen in FIGS. 5, 6 and 7. Respectively, each of these figures represents a progressive step in placing a hemostatic clip along an incision edge. In FIG. 5, the guides 28 are being used to separate the incision edge 32 from the skull 30 and to gather that section of the incision edge 32 to be hemostatically clipped. The second hemostatic clip 12 is positioned on the guides 28 such that its upper surface 12 and lower surface 42 have been forced apart by the wedges 38 and, now the upper and lower members of the guides 28. As so positioned, clip 12 is ready for placement. It is noted that the rear face 44 of the second hemostatic clip 12 is in contact with the front edge of the upper surface 46 and lower surface 48 of the third hemostatic clip 14 which, in turn, is similarly in contact with the fourth hemostatic clip 16.

Referring now to FIG. 6, a discrete forward conveying force is applied to the rear face 56 of the fourth hemostatic clip 16 by the bar plate 58 and bar 62. This force causes the second hemostatic clip 12 to be issued from the dispenser 11 and to clip the incision edge 32 at the hemostatic site 34. The upper surface 26 and lower surface 42 are normally biased against the hemostatic site 34 by the action of the rear face 44. The force which caused the second hemostatic clip 12 to issue from the end of the dispenser 11 has also positioned the third hemostatic clip 14 on the upper and lower members of the guides 28 for the next successive application to the incision edge 32. The dispenser 11 is then separated from the incision edge 32 leaving the second hemostatic clip 12 properly in place. A subsequent activation of the trigger (82 in FIG. 1) can then be used to place the third hemostatic clip 14 along the incision edge 32. Since all of the clips are properly aligned in the magazine for placement along the incision edge, a series of clips can be quickly and accurately placed along either side of the incision edge without need for the time consuming reload procedure necessary in using manually placed Raney clips.

While the subject invention has been described with reference to preferred embodiments, it will be apparent that other changes and modifications could be made by one skilled in the art, without varying from the scope or spirit of the claims appended hereto.

I claim:

1. An apparatus for dispensing jaw-type clips for use in achieving hemostasis along an incision edge, which comprises:
    (a) clips, having two opposing surfaces which form a jaw, and means to bias said surfaces together,
    (b) an elongated magazine for holding at least two of said clips, said magazine including means to direct the clips to one end thereof with the jaws of the clips in an open condition,
    (c) guides, projecting from said one end of the magazine, said guides being adapted to gather that section of the incision edge to be hemostatically clipped, and
    (d) means for conveying said clips through said magazine, toward and past said guides,
whereby in use, said guides position the incision edge between the open jaw of said clips, said conveying means pushes said clip over and past said guides, and whereupon the jaw of said clip closes around the incision edge to achieve hemostasis.

2. The apparatus of claim 1 wherein said clips have upper and lower quadrilateral surfaces which intersect at one edge to form the front of a jaw, and said surfaces are joined at their rear edges to the upper and lower edges, respectively, of a third face to form said surface biasing means.

3. The apparatus of claim 1 wherein said elongated magazine is a channel bounded by at least a lower surface and two side walls, said side walls each having a wedge attached thereto, said wedges are widest at the guide end of said magazine and run the length of the magazine to its other end where said wedges are narrowest, and wherein the clips are loaded into said other end of the magazine such that the wedges force open the clips' jaws so that as the clips are conveyed along the length of the magazine toward said guide end, their jaws are opened wider.

4. The apparatus of claim 1 wherein said conveying means comprises:
    (a) a base having a key way;
    (b) a magazine holder which is attached to said base;
    (c) an elongated bar, passing through said keyway for movement relative thereto, said bar having a plate at one end thereof received within said magazine; and
    (d) trigger operated bar forwarding means to selectively advance said bar into engagement with clips contained within the magazine, or permit said bar to be retracted for reloading of the magazine.

5. An apparatus according to claim 1 wherein said means to direct the clips to one end of the magazine includes divergent surfaces to spread the jaws of the clips as the clips are conveyed past the guides.

6. An improved method for hemostatically closing an incision in a flesh member, said improved method comprising:
    engaging the flesh member to either side of the incision with a bridge spanning the incision;
    directing a clip having normally engaged spring biased jaws over the bridge to spread the jaws of the clip; and
    releasing said clip from the bridge to engage the flesh member to either side of the incision between said jaws.

7. The improved method of claim 6 wherein said clip is directed toward, and released from, said bridge by cooperation of an elongated magazine containing said clips and means for conveying said clips through said magazine, toward and past said bridge.

8. The improved method of claim 6 wherein said incision is closed by successively repeating the improved method steps, whereby a plurality of said clips engages the flesh members on either side of the incision.

* * * * *